US009123139B2

(12) United States Patent
Murashita (10) Patent No.: US 9,123,139 B2
(45) Date of Patent: Sep. 1, 2015

(54) ULTRASONIC IMAGE PROCESSING WITH DIRECTIONAL INTERPOLATION IN ORDER TO INCREASE THE RESOLUTION OF AN IMAGE

(75) Inventor: Masaru Murashita, Mitaka (JP)

(73) Assignee: HITACHI ALOKA MEDICAL, LTD., Tokyo (JP)

( * ) Notice: Subject to any disclaimer, the term of this patent is extended or adjusted under 35 U.S.C. 154(b) by 304 days.

(21) Appl. No.: 13/211,781

(22) Filed: Aug. 17, 2011

(65) Prior Publication Data

US 2012/0053464 A1 Mar. 1, 2012

(30) Foreign Application Priority Data

Aug. 25, 2010 (JP) .................................. 2010-187874

(51) Int. Cl.
*A61B 8/00* (2006.01)
*G06T 3/40* (2006.01)
*A61B 8/08* (2006.01)

(52) U.S. Cl.
CPC .................. *G06T 3/403* (2013.01); *A61B 8/483* (2013.01); *A61B 8/00* (2013.01); *A61B 8/463* (2013.01)

(58) Field of Classification Search
CPC ........... G06T 3/403; A61B 8/00; A61B 8/463
See application file for complete search history.

(56) References Cited

U.S. PATENT DOCUMENTS

| 5,706,816 | A | 1/1998 | Mochizuki et al. |
| 6,674,879 | B1 * | 1/2004 | Weisman et al. ............. 382/128 |

(Continued)

FOREIGN PATENT DOCUMENTS

| CN | 1493258 A | 5/2004 |
| CN | 1759812 A | 4/2006 |

(Continued)

OTHER PUBLICATIONS

European Search Report dated Dec. 22, 2011, issued in corresponding European Patent Application No. 11006351.8.

(Continued)

*Primary Examiner* — Unsu Jung
*Assistant Examiner* — Serkan Akar
(74) *Attorney, Agent, or Firm* — Westerman, Hattori, Daniels & Adrian, LLP (57) ABSTRACT

In an ultrasonic image processing apparatus, an original image in the form of a three-dimensional ultrasonic image is generated from volume data based on the volume rendering method. Directional interpolation processing is then applied to the original image. More specifically, a corresponding point corresponding to a noted pixel in the display image is first determined on the original image. Then, on the original image, a plurality of candidate directions extending through the corresponding point are set, and a dispersion value is computed for each of the candidate directions. Further, a normal direction with the maximum dispersion value is specified among the candidate directions, and a reference direction along the contour of a tissue is determined in the direction orthogonal to the specified normal line. Alternatively, the reference direction is determined as a direction with the minimum dispersion value among the plurality of candidate directions. Based on a plurality of pixel values existing in the reference directions, an interpolated pixel value of the noted pixel is computed. Contrast emphasis processing is further applied following the directional interpolation processing, as required.

8 Claims, 11 Drawing Sheets

(56) References Cited

U.S. PATENT DOCUMENTS

| | | | |
|---|---|---|---|
| 2004/0081340 A1 | 4/2004 | Hashimoto | |
| 2005/0054924 A1* | 3/2005 | Dione et al. | 600/437 |
| 2005/0267366 A1 | 12/2005 | Murashita et al. | |
| 2006/0103670 A1 | 5/2006 | Matsumoto | |
| 2006/0139361 A1 | 6/2006 | Busch et al. | |
| 2007/0173723 A1 | 7/2007 | Kanda et al. | |
| 2008/0123992 A1 | 5/2008 | Tian et al. | |
| 2008/0123998 A1 | 5/2008 | Gomi et al. | |
| 2009/0054778 A1* | 2/2009 | Pagoulatos et al. | 600/443 |

FOREIGN PATENT DOCUMENTS

| | | |
|---|---|---|
| CN | 101190132 A | 6/2008 |
| EP | 0565948 A2 | 10/1993 |
| JP | 09-330399 A | 12/1997 |
| JP | 10-033538 A | 2/1998 |
| JP | 2002-312809 A | 10/2002 |
| JP | 2005-332130 A | 12/2005 |
| JP | 2006-136619 A | 6/2006 |
| JP | 2006-271594 A | 10/2006 |
| JP | 2006-526834 A | 11/2006 |
| JP | 2007-312880 A | 12/2007 |
| JP | 2010-000125 A | 1/2010 |

OTHER PUBLICATIONS

Thurnhofer, Stefan et al.; "Edge-Enhanced Image Zooming"; Optical Engineering, Soc. of Photo-optical Instrumentation Engineers, Bellingham, vol. 35, No. 7, Jul. 1, 1996, pp. 1862-1869. (cited in European Search Report dated Dec. 22, 2011).

Wang, Yao et al.; "Edge Preserved Image Zooming"; Signal Processing: Theories and Applications. Grenoble, Sep. 5-8, 1988; Proceedings of the European Signal Processing Conference (EUSIPCO), Amsterdam, North Holland, NL, vol. 3, Sep. 5, 1988, pp. 1445-1448. (cited in European Search Report dated Dec. 22, 2011).

Eurooean Office Action dated Mar. 19, 2013, issued in corresponding European Patent Application No. 11 006 351.8 (7 pages).

Steen E et al., "vol. Rendering of 3D Medical Ultrasound Data Using Direct Feature Mapping", IEEE Transactions on Medical Imaging, IEEE Service Center, Piscataway, NJ, US, vol. 13, No. 3, Sep. 1, 1994, pp. 517-525, XP000474142.

European Office Action dated Dec. 5, 2013 issued in corresponding European Application No. 11 006 351.8.

Kajiya J. T. et al: "Ray Tracing vol. Densities", Proceedings of the Siggraph '84, ACM, NY, USA, vol. 18, No. 3, Jul. 1984, pp. 165-174.

Chinese Office Action dated Jan. 6, 2014, issued in corresponding Chinese application No. 2011102514063, w/ English translation (13 pages).

Japanese Office Action dated Feb. 25, 2014, issued in corresponding Japanese application No. 2010-187874, w/ partial English translation (6 pages).

Fenster et al., "3-D Ultrasound Imaging: A Review", IEEE Engineering in Medicine and Biology Magazine, IEEE Service Center, Piscataway, NJ, US, Nov. 1, 1996, vol. 15, No. 6, pp. 41-51, Communication pursuant to Article 94(3) EPC dated Mar. 17, 2015, issued in corresponding Patent Application No. 11 006 351.8.

Sakas, et al., "Preprocessing and Volume Rendering of 3D Ultrasonic Data", IEEE Computer Graphics and Applications, IEEE Service Center New York, NY, US, Jul. 1, 1995, vol. 15, No. 4, pp. 47-54, Communication pursuant to Article 94(3) EPC dated Mar. 17, 2015, issued in corresponding Patent Application No. 11 006 351.8.

Gibbs, "A Great Leap in Graphics", Scientific American, Aug. 2006, vol. 295, No. 2, pp. 80-84, Communication pursuant to Article 94(3) EPC dated Mar. 17, 2015, issued in corresponding Patent Application No. 11 006 351.8.

Communication pursuant to Article 94(3) EPC dated Mar. 17, 2015, issued in corresponding Patent Application No. 11 006 351.8 (12 pages).

\* cited by examiner

ULTRASONIC IMAGE PROCESSING WITH DIRECTIONAL INTERPOLATION IN ORDER TO INCREASE THE RESOLUTION OF AN IMAGE

BACKGROUND

1. Field of the Invention

The present invention relates to an ultrasonic image processing apparatus, and more particularly to technology for enhancing the image quality of a three-dimensional ultrasonic image.

2. Description of Related Art

An ultrasonic image processing apparatus is an apparatus which forms an ultrasonic image based on data acquired by transmission and reception of ultrasound or which processes such an ultrasonic image, and is configured as an ultrasonic diagnosis apparatus or an information processing apparatus. Here, an information processing apparatus is a computer which processes data transmitted from an ultrasonic diagnosis apparatus, for example. In an ultrasonic image processing apparatus, an ultrasonic image to be formed or to be processed includes a two-dimensional ultrasonic image, a three-dimensional ultrasonic image, or the like.

By applying a volume rendering method to volume data (a set of echo data) acquired from a three-dimensional space within a living organism (a living body), a three-dimensional ultrasonic image (a volume rendering image) is formed. More specifically, first, a plurality of rays (virtual lines of sight, which correspond to an operation path) extending from a point of view are set with respect to the volume data, and then a predetermined operation is executed in a repeated manner sequentially for sample points existing on each of the rays, thereby obtaining a pixel value for each ray. Finally, a three-dimensional image is formed as a set of a plurality of pixel values corresponding to the plurality of rays. (See JP 10-33538 A, for example.)

The algorithm of general volume rendering is expressed by the following formula. In the following formula, I represents a pixel value (a brightness value), $e(i)$ represents an echo intensity (an echo value) on a sample point on a ray, and $o(e(i))$ represents the opacity (a degree of opaqueness), in which i represents the number of a sample point.

$$I = \Sigma [e(i) * o(e(i)) * (1 - o\_out(i-1))] \quad (1)$$

wherein $o\_out(i) = \Sigma o(e(i)) * (1 - o\_out(i-1))$

Here, the operation is completed when the sum of the opacities reaches 1 or when the sample point is outside the operation range, and the value of I at this time is mapped on a projection plane. The above formula (1) is only an example, and various other algorithms for the volume rendering processing are known.

Here, as the display methods for a three-dimensional image, there are known a four-view display in which four images are displayed within a single screen (e.g. display of three orthogonal cross-sectional images and a 3D image), a two-view display in which two images are displayed within a single screen (e.g. display of a cross-sectional image and a 3D image), a one-view display in which a single image is displayed within a single screen (e.g. display of a 3D image), or the like. As the time required for processing single volume data is generally in proportion to the number of pixels on the projection plane (i.e. the number of rays), among the three methods described above, the one-view display method requires the longest processing time. The larger the monitor size, as the number of pixels forming the display image increases, the processing time becomes longer accordingly.

As such, in general, there is a problem concerning formation of a three-dimensional image in that the amount of computation is large and the burden on the CPU is large. While the use of high-speed processors can be considered, in this case, another problem of increased cost would also arise.

While it is desirable to reduce the number of rays to thereby decrease the amount of computation in order to deal with the above problems, if the number of rays is simply decreased, the resolution of the three-dimensional image is lowered or the size of the three-dimensional image is reduced. Application of linear interpolation processing can therefore be considered. With the linear interpolation processing, it is possible to increase the apparent number of pixels and the resolution. This processing, however, causes the image to be blurred, which leads to a problem of a reduction in image quality. The problem of reduction in image quality would also arise when an image is simply enlarged.

It is generally pointed out that a three-dimensional ultrasonic image generated by the volume rendering method lacks sharpness and has unclear contours. Here, the conventional general interpolation processing references four, eight, or sixteen vicinity pixels existing around a noted pixel. In other words, in the conventional general interpolation processing, the range to be referenced extends equally in all directions around the noted pixel. In the conventional art, it is not possible to adaptively change the interpolation condition in accordance with the structure of a tissue.

JP 2010-125 A discloses an apparatus for forming an image of cartilage included in the knee joint. This reference describes, starting from paragraph 0042, the contents of pre-processing which is executed prior to the cartilage image forming processing. The pre-processing is executed in units of slice data (two-dimensional frames). More specifically, among a plurality of line segments extending through a noted pixel, a line segment having the maximum dispersion value is specified and a line segment which is orthogonal to that specified line segment is further specified. Then, an average value of a plurality of pixel values existing on that orthogonal line segment is calculated and is used as an updated pixel value for the noted pixel. This processing is applied to each slice data before formation of a cartilage image, and therefore is not processing which is applied to a 3D image after the volume rendering. Further, JP 2010-125 A does not describe special directional interpolation processing having a magnification changing function (a resolution changing function).

SUMMARY OF THE INVENTION

An advantage of the present invention is to enhance the image quality of a three-dimensional ultrasonic image or to reduce the amount of computation for generating a three-dimensional ultrasonic image.

Another advantage of the present invention is to enable formation of a three-dimensional ultrasonic image having excellent image quality even when the number of rays is small.

In accordance with an aspect of the present invention, an apparatus of the present invention includes a rendering unit which sets a plurality of rays with respect to volume data acquired from a three-dimensional space within a living organism and executes a rendering operation along each ray to generate an original image in the form of a three-dimensional image, and a directional interpolation processing unit which generates a display image based on the original image, the directional interpolation processing unit applying directional interpolation processing based on the original image to each of noted pixels forming the display image to thereby generate an interpolated pixel value for the noted pixel, wherein with the directional interpolation processing, a pixel reference direction for computing the interpolated pixel value is determined in a direction of flow of a tissue which is three-dimensionally represented in the original image.

With the above structure, an original image is first generated in the form of a three-dimensional image by volume rendering processing, and then, directional interpolation processing is applied to the original image to generate a display image based on the original image. The directional interpolation processing is not processing which equally references a whole region around a corresponding point (a point of interest) serving as a center, but is processing which determines a pixel reference direction in the direction of flow of a tissue and computes an interpolated pixel value by using a plurality of pixel values arranged in the pixel reference direction. Accordingly, with this processing, the contour of a tissue can be clarified, so that blurring generated on the three-dimensional image can be improved. Stated inversely, even if the number of rays is reduced to form a three-dimensional image having low resolution, by applying the directional interpolation processing to the three-dimensional image in an ex-post manner, a three-dimensional image of high resolution can be generated. As such, the reduction in the amount of computation and the enhancement of the image quality can be accomplished simultaneously. Preferably, the display image is an image having a magnification or a resolution which is different from a magnification or a resolution of the original image, and the magnification or the resolution is changed at the time of the directional interpolation processing.

Preferably, the directional interpolation processing unit includes an evaluation value computation unit which sets a plurality of mutually different candidate directions on the original image, using a corresponding point corresponding to the noted pixel as a reference, and computes an evaluation value indicating a variation in pixel values in each of the candidate directions; a direction determination unit which determines the pixel reference direction based on a plurality of evaluation values which are computed; and an interpolated pixel value computation unit which computes the interpolated pixel value based on a plurality of pixel values concerning a plurality of pixels arranged in the pixel reference direction. The pixel reference direction is a direction along a contour (boundary) of a tissue. It is possible to either obtain a normal direction with respect to the contour first and then determine the pixel reference direction which is orthogonal to the normal direction, or to directly determine the pixel reference direction as a direction parallel to the contour. In the former case, the pixel reference direction may be determined by specifying a candidate direction with the maximum dispersion value among a plurality of candidate directions and determining the direction orthogonal to the specified direction. In this case, the pixel reference direction may be determined as one of the plurality of candidate directions, or the pixel reference direction may be determined between two candidate directions. Alternatively, the pixel reference direction may be determined as a direction with the minimum dispersion value among the plurality of candidate directions.

Preferably, as a result of applying the directional interpolation processing to each of pixels forming the display image, the display image corresponding to an enlarged image of the original image is generated, and an enlargement ratio of the display image is determined based on the number of rays which is set for generating the original image. As the number of pixels forming a three-dimensional image is determined in accordance with the number of images (the number of views) which are displayed simultaneously in a single screen, it would be desirable to first determine the number of rays corresponding to the smallest image and, when it becomes necessary to display a larger image, to increase the magnification in the direction interpolation processing in accordance with a ratio of change of the size. In other words, the magnification may be changed in accordance with the number of views, with the number of rays being fixed independently of the number of views.

Preferably, a post processing unit which applies post processing to the display image which is generated by the directional interpolation processing is further provided, and the post processing is processing for adjusting a contrast of the display image.

Preferably, with the contrast adjusting processing, when an input pixel value is greater than a background average brightness value, based on the input pixel value, an output pixel value which is greater than the input pixel value is output, and when an input pixel value is smaller than the background average brightness value, based on the input pixel value, an output pixel value which is smaller than the input pixel value is output.

A program according to the present invention is an ultrasonic image processing program which is executed in an information processing apparatus and includes a module which sets a plurality of rays with respect to volume data acquired from a three-dimensional space within a living organism and executes a rendering operation along each ray, to thereby generate an original image in the form of a three-dimensional image; and a directional interpolation processing module which generates a display image based on the original image, the directional interpolation processing module applying directional interpolation processing on the basis of the original image to each of noted pixels forming the display image to generate an interpolated pixel value for the noted pixel, and the directional interpolation processing includes processing of setting a plurality of mutually different candidate directions on the original image, using a corresponding point corresponding to the noted pixel as a reference, and computing an evaluation value indicating a variation in pixel values in each of the candidate directions, processing of determining a pixel reference direction for computing an interpolated pixel value from among the plurality of candidate directions, based on a plurality of evaluation values which are computed, and processing of computing the interpolated pixel value based on a plurality of pixel values concerning a plurality of pixels arranged in the pixel reference direction. In the directional interpolation processing, the pixel reference direction is determined in a direction of flow of a tissue which is three-dimensionally represented in the original image. The information processing apparatus may be a computer, an ultrasonic diagnostic apparatus, or the like. The directional interpolation processing may be treated as independent processing. The above-described program can be stored in a recording medium such as a CD-ROM, and can be installed in an information processing apparatus via such a recording medium.

BRIEF DESCRIPTION OF THE DRAWINGS

A preferred embodiment of the present invention will be described in detail by reference to the following figures, wherein.

DESCRIPTION OF EMBODIMENTS

A preferred embodiment of the present invention will be described in detail with reference to the accompanying drawings.

Figure 1:
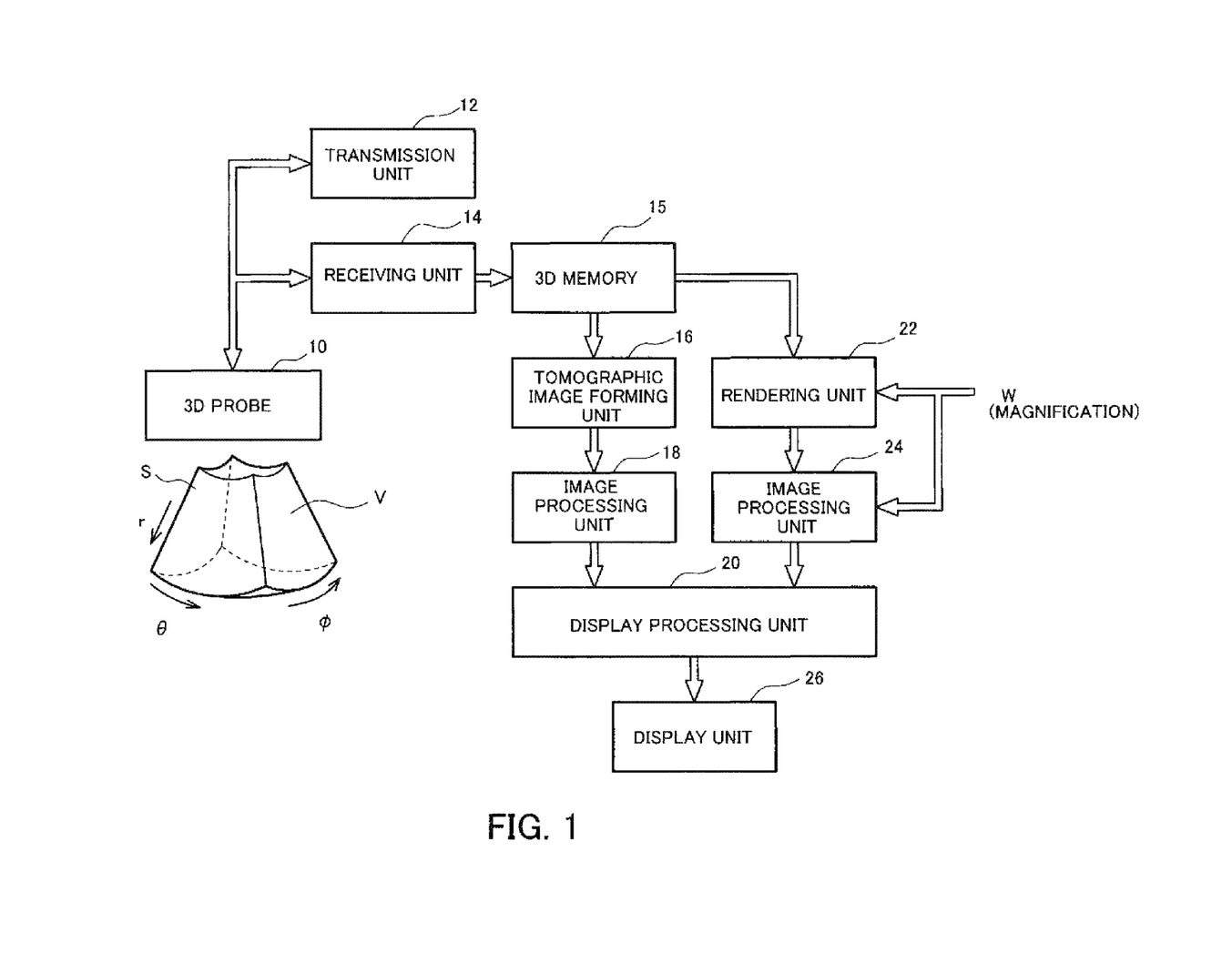
FIG. 1 is a block diagram illustrating the whole structure of an ultrasonic diagnosis apparatus according to the present invention.

FIG. 1 is a block diagram illustrating the whole structure of a preferred embodiment of an ultrasonic image processing apparatus according to the present invention. In the present embodiment, the ultrasonic image processing apparatus is configured as an ultrasonic diagnosis apparatus.

More specifically, an ultrasonic diagnosis apparatus is an apparatus which is used in the medical field and forms an ultrasonic image by transmission and reception of ultrasound to and from a living organism. In the present embodiment, ultrasound is transmitted and received with respect to a three-dimensional region within a living organism, thereby acquiring volume data. Based on the volume data which are acquired, a three-dimensional ultrasonic image serving as a volume rendering image or one or more tomographic images are formed, as will be described in detail below.

A 3D probe 10 is an ultrasonic probe for capturing three-dimensional echo data. In the present embodiment, the 3D probe 10 includes a 1D array transducer and a mechanical scanning mechanism for mechanically scanning the 1D array transducer. The 1D array transducer is formed of a plurality of transducer elements which generate an ultrasonic beam. The ultrasonic beam is then electronically scanned in the element arrangement direction, thereby forming a scan plane. When the 1D array transducer is mechanically scanned, the scan plane is moved in a swinging manner so that a three-dimensional space is formed. In FIG. 1, "r" indicates a depth direction, "θ" indicates an electronic scanning direction of the ultrasonic beam, "φ" indicates a mechanical scanning direction of the scan plane, "S" indicates the scan plane, and "V" indicates a three-dimensional space. Instead of the mechanical scanning method described above, a 2D array transducer may be used to electronically scan an ultrasonic diagnosis apparatus beam in a two-dimensional manner.

The 3D probe 10 has a transmission/reception plane which is brought into contact with a surface of the living organism. In the present embodiment, the 3D probe 10 is brought into contact with the abdomen of a pregnant woman. A transmission unit 12, which is a transmission beam former, supplies a plurality of transmission signals having a predetermined delay relationship to the plurality of transducer elements, thereby forming a transmission beam. At the time of reception, echoes from within the living organism are received by the plurality of transducer elements, which then output a plurality of reception signals to a receiving unit 14. The receiving unit 14 is a receiving beam former; i.e., a phase alignment and summation processing unit in which delay processing is applied to the plurality of reception signals and the plurality of delayed reception signals are summed. Consequently, a receiving beam is electronically formed and a reception signal (beam data) after the phase alignment and summation processing corresponding to the receiving beam is output. The beam data are stored in a 3D memory 15.

The 3D memory 15 includes a storage space (data processing space) corresponding to a three-dimensional space (actual space) in the living organism. Specifically, each echo data item forming the beam data is mapped to a corresponding address within the storage space. With the writing of the data in the 3D memory 15, coordinates conversion processing is applied, or with the reading of the data from the 3D memory 15, coordinates conversion processing is applied.

A tomographic image forming unit 16 is a module which forms one or a plurality of tomographic images corresponding to one or a plurality of cross-sectional planes which are set with respect to the three-dimensional space. Each tomographic image is a monochrome B-mode image. The position of each cross sectional plane can be arbitrarily set by a user. The tomographic image forming unit 16 reads a set of echo data corresponding to the cross sectional planes which are thus set from the 3D memory and forms a tomographic image based on the read data. The tomographic image which is formed is output to a display processing unit 20 via an image processing unit 18. The image processing unit 18 has various image processing functions which may include directional (or anisotropic) interpolation processing which will be described below. The display processing unit 20 synthesizes a plurality of images to form a single display image and outputs image data representing the display image to a display unit 26.

A rendering unit 22 is a module which executes volume rendering processing. Specifically, the rendering unit 22 executes processing for forming a three-dimensional image by using the volume data which are read from the 3D memory 15. A variety of algorithms have been proposed as rendering methods. More specifically, the rendering unit 22 sets a plurality of rays with respect to the volume data and executes a rendering operation for each ray, thereby computing pixel values. Thus, a three-dimensional image (original image) is generated as a set of a plurality of pixel values. At this time, a magnification W is referenced, and the number of rays is determined based on the magnification W. In the present embodiment, the rays are basically thinned out as compared with the conventional art. In other words, according to the present embodiment, the original image having low resolution is generated with a small number of rays, and then post processing is performed with respect to the original image to thereby form a display image having high resolution.

An image processing unit 24 is a module which executes the directional interpolation processing. More specifically, the image processing unit 24 also performs change of the magnification (resolution) simultaneously with the interpolation processing, as will be described in detail below. In any case, by applying such directional interpolation processing to the original image, it is possible to generate a display image having an emphasized clear contour, whose resolution or magnification has been changed. Post processing may be further applied to such a display image, as required. In the present embodiment, contrast emphasis processing is applied as the post processing. The image having been subjected to such processing is transmitted to the display processing unit 20. When operations are performed by the image processing unit 24, the magnification W is referenced as required.

In FIG. 1, each of the functions illustrated in the stages after the 3D memory 15 is implemented as software processing. A control unit which is formed of a CPU and an operation program is omitted in FIG. 1. The directional interpolation processing and the rendering processing described above may be executed by an information processing apparatus such as a computer. In this case, the volume data supplied from the ultrasonic diagnosis apparatus on-line or off-line is processed by such an information processing apparatus.

Figure 2:
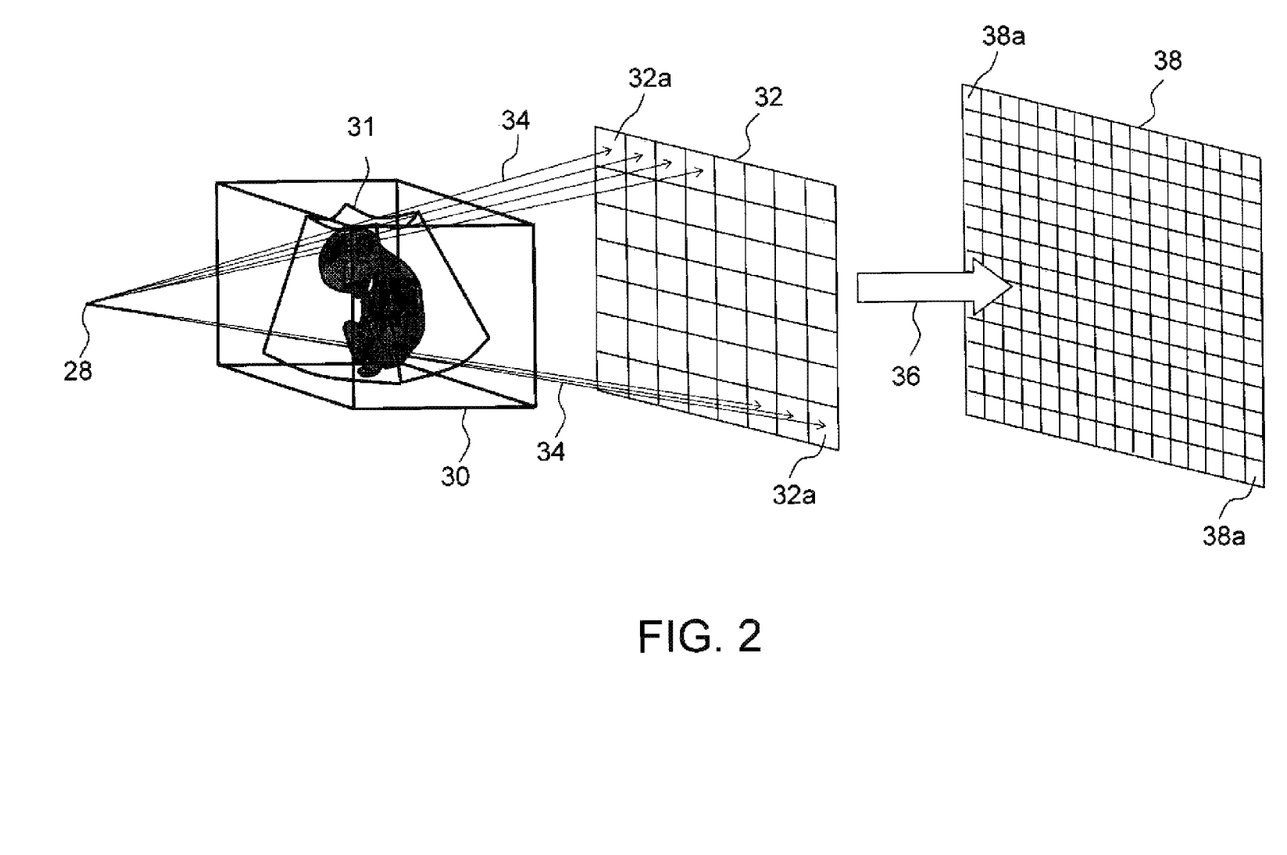
FIG. 2 is a view conceptually illustrating volume rendering and directional interpolation processing.

FIG. 2 illustrates the rendering processing and the directional interpolation processing. Reference numeral 30 designates a storage space corresponding to a three-dimensional space within a living organism, and in this storage space 30, volume data 31, which in this embodiment are volume data of a fetus, are present. A point of view 28 is set at an arbitrary position with respect to the storage space 30 or the volume data 31. Further, a plurality of rays (lines of sight) 34 originating from the point of view 28 are determined. In this case, a plurality of rays 34 are set so as to extend through the volume data 31. A screen 32 is a projection plane, and a plurality of pixels on the screen 32 correspond to the plurality of rays on a one-to-one basis. In this illustrated example, reference numeral 32a indicates a pixel. The rendering operation; i.e., the voxel operation, is executed along each ray sequentially concerning a plurality of voxels (sample points) existing on each ray, and a brightness value serving as a final operation result is mapped as a pixel value of a pixel corresponding to that ray. By repeating this operation for each ray, the original image (a three-dimensional image) is formed as a set of a plurality of pixel values.

According to the present embodiment, the directional interpolation processing; i.e., special post processing, which is designated by numeral reference 36, is applied to such an original image. Consequently, it is possible to form a display image having a high resolution on a display plane 38. Here, reference numeral 38a designates pixels forming the display plane 38. On the display plane 38, a display image in the form of a three-dimensional image, which is enlarged or whose resolution has been increased, is formed. In this embodiment, with the directional interpolation processing which is performed as such post processing, an apparent resolution can be increased and also the contours can be clarified. Accordingly, under the precondition that such post processing is to be executed, a speedy rendering operation can be performed by reducing the number of rays in the volume rendering, to thereby lessen the processing load. Specifically, as will be described below, after the number of rays is first set based on a small three-dimensional image in four-view display as a precondition, the magnification during the directional interpolation processing is increased, so that a large image can be formed. With this method, one-view display can be achieved with an amount of three-dimensional computation which is similar to that for a four-view image.

Figure 3:
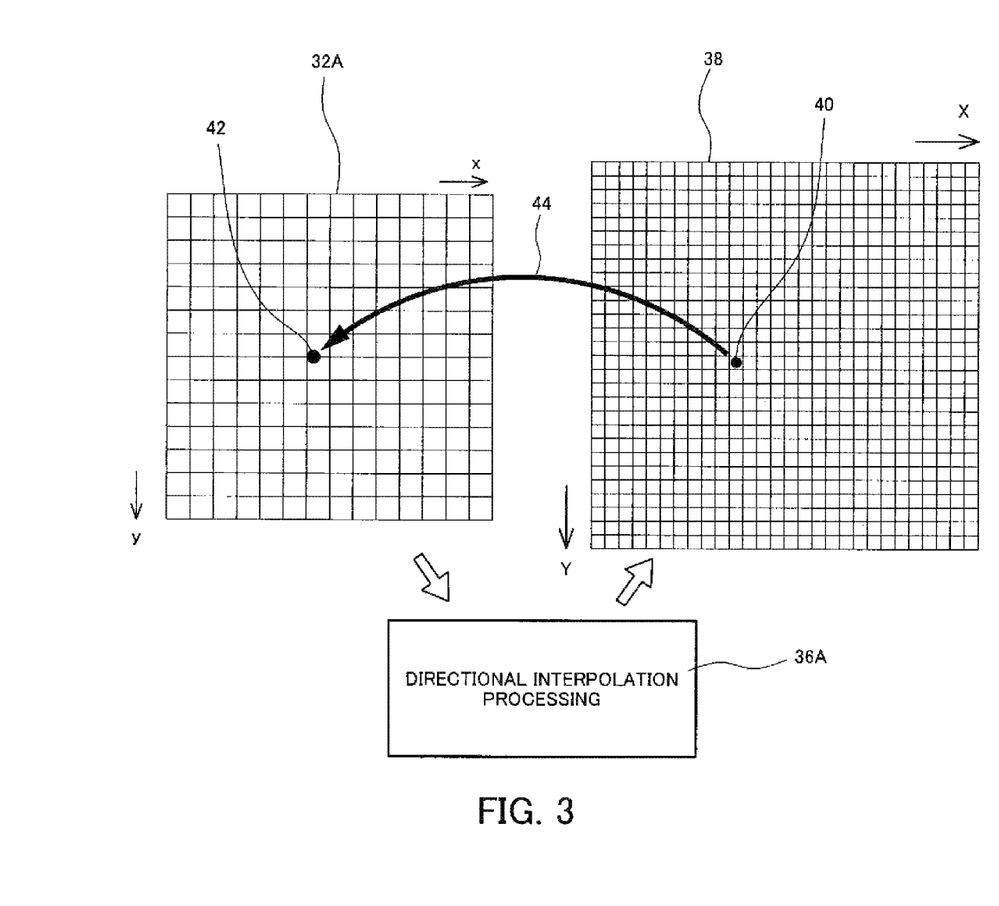
FIG. 3 is a conceptual view illustrating the content of the directional interpolation processing.

FIG. 3 illustrates a concept of the directional interpolation processing 36A. In FIG. 3, a view on the left side illustrates an original image 32A, and an image on the right side illustrates a display image (display plane) 38. With the directional interpolation processing 36A performed based on the original image 32A, the display image 38 which is enlarged or whose resolution has been increased can be formed. More specifically, each of pixels forming the display image 38 is sequentially determined as a noted point 40. As illustrated by reference numeral 44, a corresponding point (a point of interest) 42 corresponding to a noted point 40 is determined on the original image 32A. Then, by applying the processing illustrated in FIGS. 4 to 6, which will be described below, an interpolated pixel value concerning the noted point is finally obtained, and is mapped as a value of the noted point 40.

Figure 4:
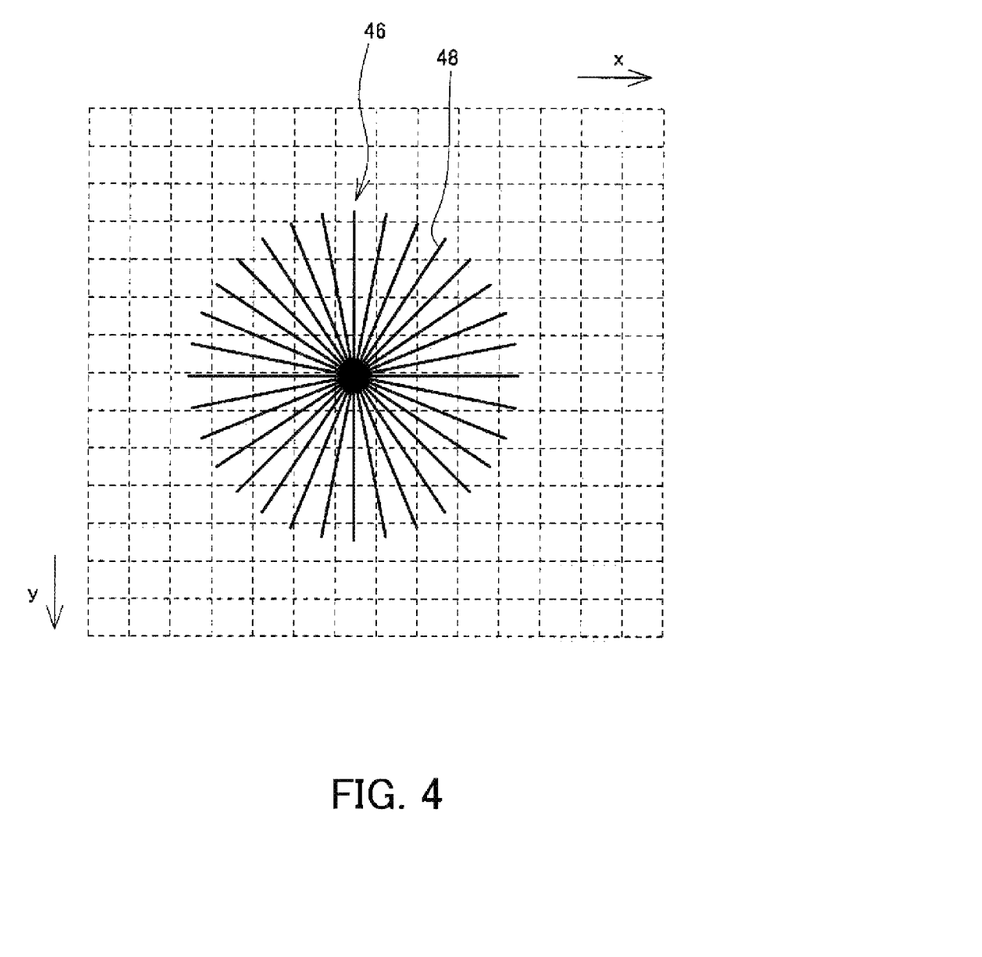
FIG. 4 is a view illustrating a plurality of candidate lines which are set with respect to a corresponding point.
Figure 5:
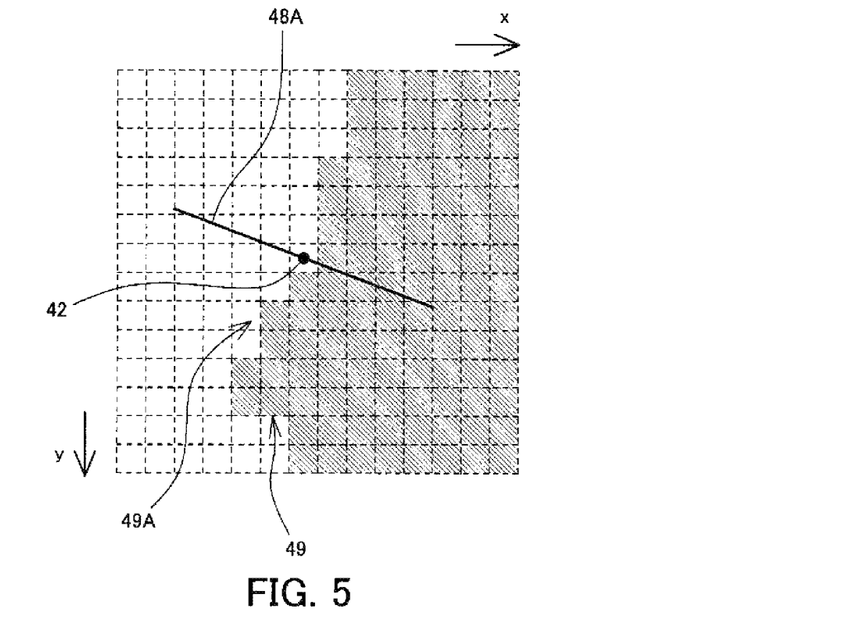
FIG. 5 is a view illustrating a normal line which is orthogonal to a contour direction.
Figure 6:
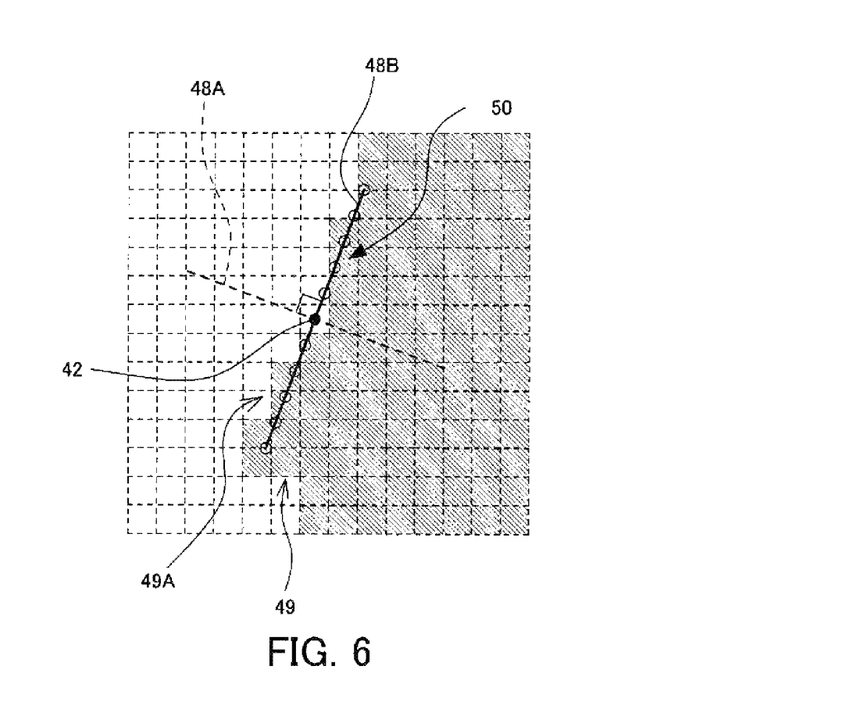
FIG. 6 is a view illustrating a reference line which is orthogonal to the normal line.

More specifically, FIG. 4 illustrates an original image and also illustrates a group of candidate lines 46 extending through the corresponding point. The group of candidate lines 46 is formed of a plurality of candidate lines arranged in radial directions, and the angle pitch between two adjacent candidate lines is uniform, and all the candidate lines have the same length. As a matter of course, uneven pitches may be adopted or the length of each line may be set adaptively. After setting the group of candidate lines 46 as described above, for each candidate line 48, with reference to a plurality of pixel values existing on that candidate line 48, a dispersion value is computed based on these pixel values. Specifically, an evaluation value indicating the degree of variation of the pixel values is computed. After a plurality of dispersion values corresponding to the plurality of candidate lines are computed, a candidate line having the maximum value among these values is determined as illustrated in FIG. 5. In the example illustrated in FIG. 5, such a candidate line is represented as a normal line 48A. Specifically, the normal line 48A is set in a direction substantially orthogonal to a peripheral edge 49A of a tissue 49 such that the normal line 48A extends through the corresponding point 42. Then, as illustrated in FIG. 6, a reference line 48B is further set as a line which is orthogonal to the normal line 48A. The reference line 48B is a line along (parallel to) the peripheral edge 49A. Further, a plurality of sampling points; i.e., a line of sampling points 50 existing on such a reference line 48B, are determined, and with reference to a plurality of pixel values of these sampling points, an interpolated pixel value is computed as an average value or a weighted average value. Specifically, such an interpolated pixel value is a brightness value corresponding to the corresponding point 42; more specifically, an interpolated pixel value of the noted point 40 illustrated in FIG. 3.

As described above, in spite of referring to the surroundings of a noted point or a corresponding point uniformly, by referring to a plurality of pixel values along the direction of a flow of tissue and obtaining an interpolated pixel value based on the plurality of pixel values, there can be formed a three-dimensional ultrasonic image with an emphasized contour or a clarified contour. Further, as described above, the advantage that, even in the case of generating an original image with low resolution by reducing the number of rays, a three-dimensional image having high resolution can be formed based on such an original image in an ex-post manner, can be achieved. Although, in the example described above, after the normal line is determined from among the plurality of candidate lines the reference line which is orthogonal to the normal line is obtained, it is also possible to specify the minimum dispersion value from among a plurality of dispersion values and then determine a candidate line having the minimum dispersion value as the reference line. In either case, it is desirable to set a plurality of search lines using a corresponding point or a noted point as a center and evaluate these lines individually, and then determine the direction of the flow of tissue as the evaluation result.

Figure 7:
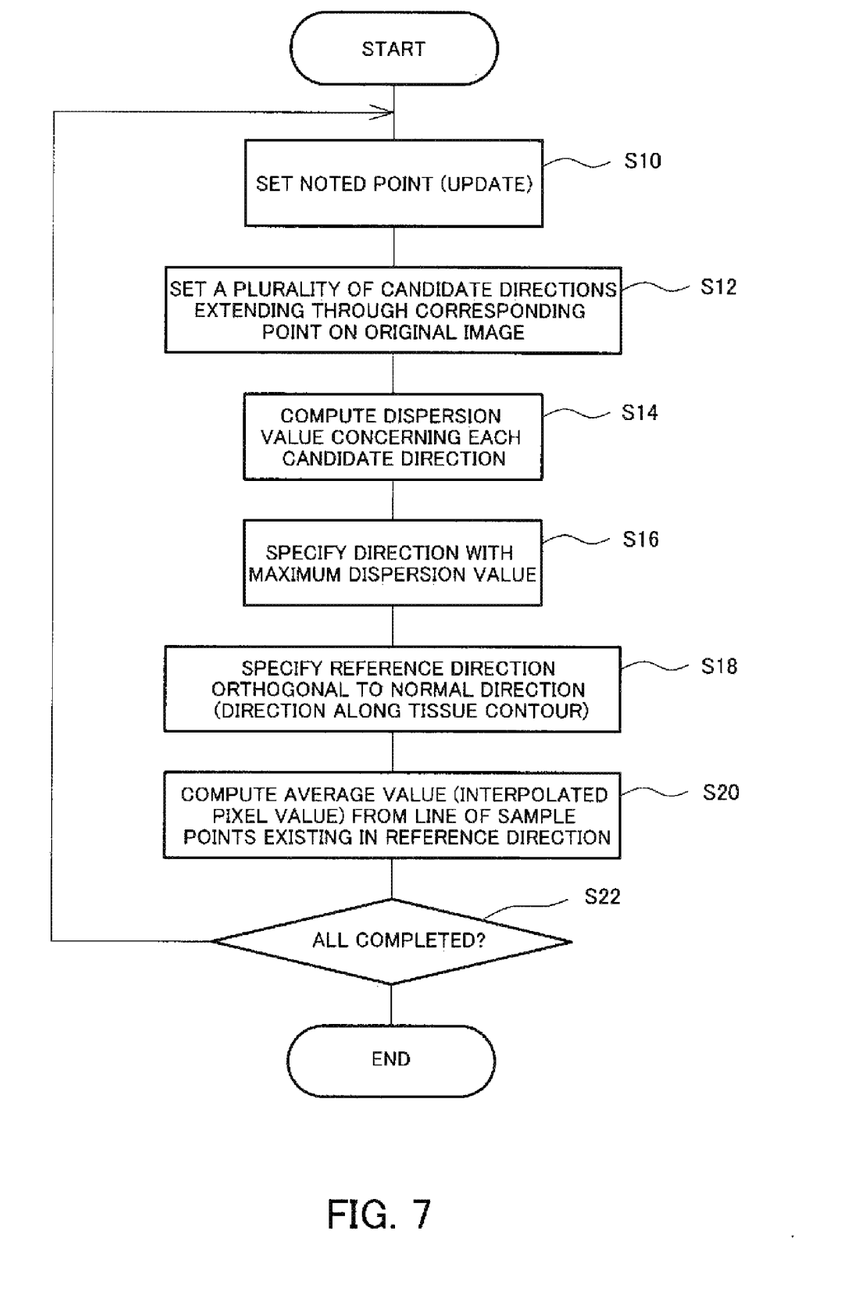
FIG. 7 is a flow chart illustrating the content of the directional interpolation processing.

FIG. 7 illustrates a flowchart for explaining the procedure described above. Specifically, a noted point is set on the display image in step S10, and in step S12 a corresponding point thereof is determined on the original image and a plurality of candidate directions extending through the corresponding point are set. In step S14, a dispersion value is computed for each of the candidate directions. Then, the candidate direction with the maximum dispersion value is specified as the normal direction in step S16, and further, the reference direction, which is orthogonal to the normal direction, is determined in step S18. The reference direction is a direction along the contour of a tissue. As described above, as a matter of course, following step S14, the reference direction may be directly specified by determining the direction with the minimum dispersion value. In step S20, with reference to a plurality of pixel values concerning a plurality of sampling points existing in the reference direction, an interpolated pixel value is computed as an average value or a weighted average value thereof. In this case, a single line of pixel values existing in the reference direction may be referenced or a plurality of lines may be referenced. Specifically, the interpolated pixel value may be obtained by setting a window extending in a rectangular shape and referencing the pixel values in the window.

Figure 8:
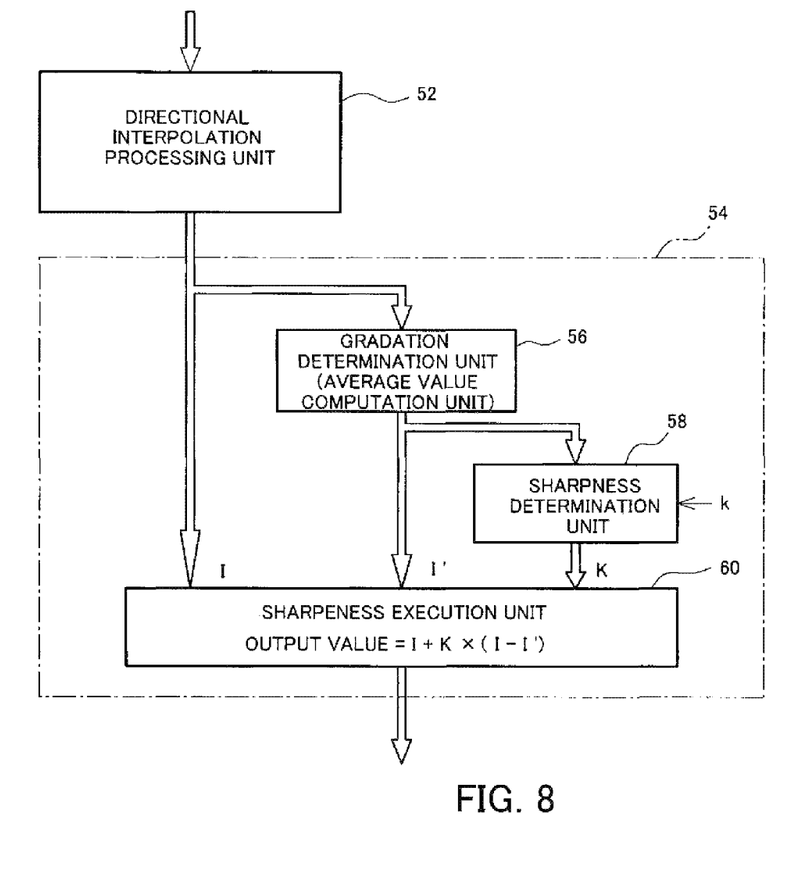
FIG. 8 is a view illustrating the directional interpolation processing performed as post processing and the following contrast emphasis processing.

FIG. 8 illustrates a plurality of post processing operations to be applied in stages. In the first stage, directional interpolation processing is applied, as indicated by a directional interpolation processing unit 52. In the second stage, contrast emphasis processing is applied, as indicated by a contrast emphasis processing unit 54. The contrast emphasis processing unit 54 includes a gradation determination unit 56, a sharpness determination unit 58, and a sharpness execution unit 60. The gradation determination unit 56 is a module which computes an average value within a window having m×m pixels, for example. The sharpness determination unit 58 is a module which computes a weight K based on the dispersion value within that window. The function which is used for computing the weight K will be described below with reference to FIG. 9. The sharpening execution unit 60 obtains a pixel value as an output value, based on the pixel value I of a pixel which is currently being noted and the average value I' within the window, and further in consideration of the weight K. More specifically, I+K×(I−I') is computed. This computation is processing in which, if the brightness value of the noted pixel value is greater than the background average brightness value, the brightness value is increased, whereas if the brightness value of the noted pixel value is smaller than the background average brightness value, the brightness value is decreased. However, as it is desirable that the brightness value is not changed greatly in the situation in which the dispersion value is great, the weight K is applied as a suppression coefficient.

Figure 9:
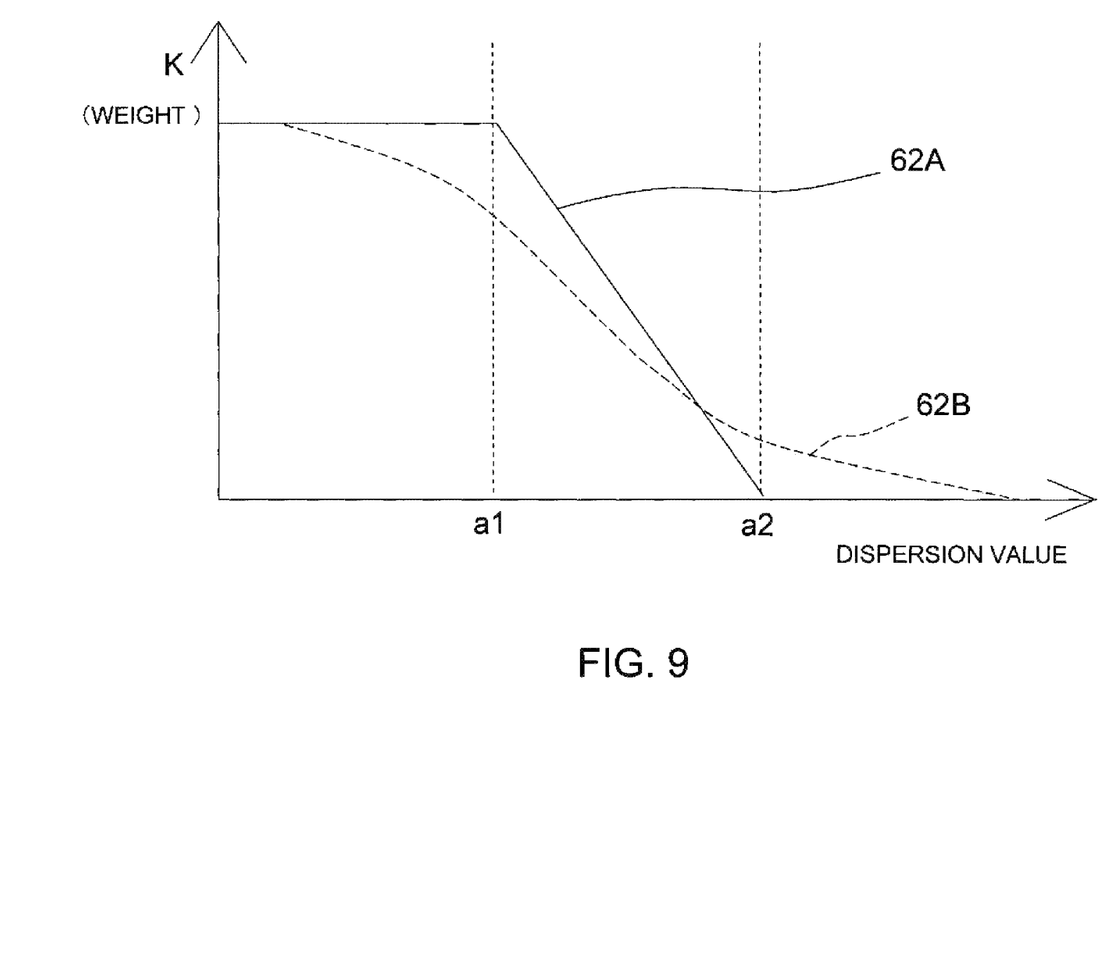
FIG. 9 is a view for explaining determination of weight K based on a dispersion value.

More specifically, the weight K is determined according to the function 62A illustrated in FIG. 9, for example. In FIG. 9, the horizontal axis represents a dispersion value and the vertical axis represents the weight K. When the dispersion value is a1 or smaller, K=1.0, for example, is set as the weight, and when the dispersion value is within the range between a1 and a2, greater the dispersion value, the smaller the weight K. Further, when the dispersion value is a2 or greater, the weight K is set to 0. With this structure, when the dispersion value is low, the contrast is emphasized, and as the dispersion value increases, such emphasis processing is reduced, and finally no emphasis processing is performed. As a matter of course, such a function 62A is only one example, and the function as indicated by reference numeral 62B can also be used. Here, as illustrated in FIG. 8, for computation of the weight K, it is also possible to increase and decrease the parameter k to thereby allow the user to vary the function shape. For example, such a parameter k is a coefficient to be multiplied by a dispersion value.

Figure 10:
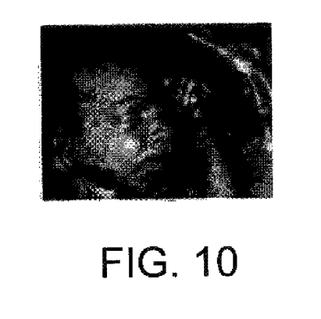
FIG. 10 is a view illustrating an original image.
Figure 11:
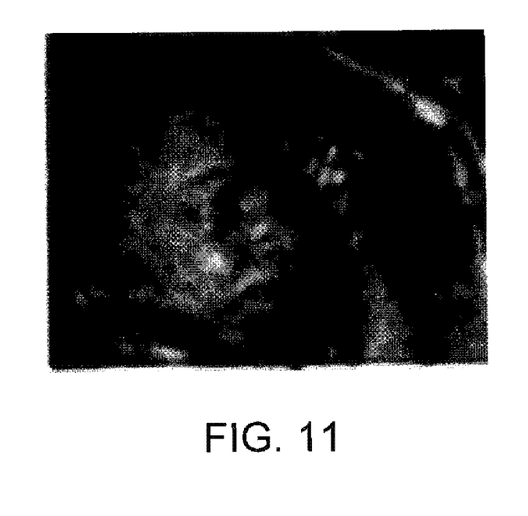
FIG. 11 is a view illustrating a result of conventional linear interpolation processing.
Figure 12:
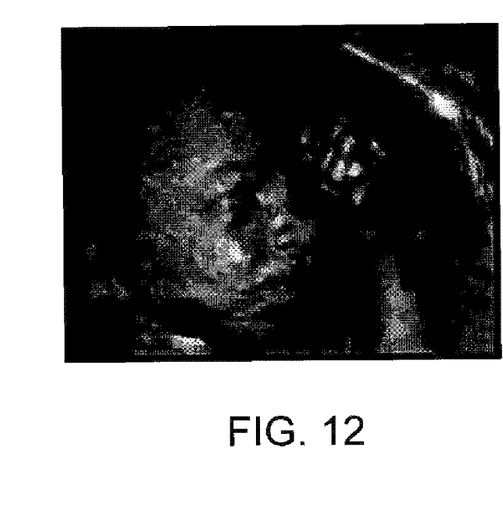
FIG. 12 is a view illustrating a result of the directional interpolation processing according to the present embodiment.

FIG. 10 illustrates an original image, and FIG. 11 illustrates a result to which conventional linear interpolation processing has been applied to the original image. For the linear interpolation processing, the magnification has been changed. As illustrated in FIG. 11, when non-directional general linear interpolation processing is applied, the image quality is significantly lowered. In other words, the image content is blurred. FIG. 12 illustrates a result in which the directional interpolation processing is applied to the original image. As illustrated in FIG. 12, the image quality of the original image is maintained even with the change of magnification, and the image content is rather made superior, in that the contour of a fetus is clearly displayed. Stated inversely, on the precondition that such post processing is to be performed, rapid three-dimensional image formation can be performed even when the number of rays is reduced to decrease the amount of computation.

Figure 13:
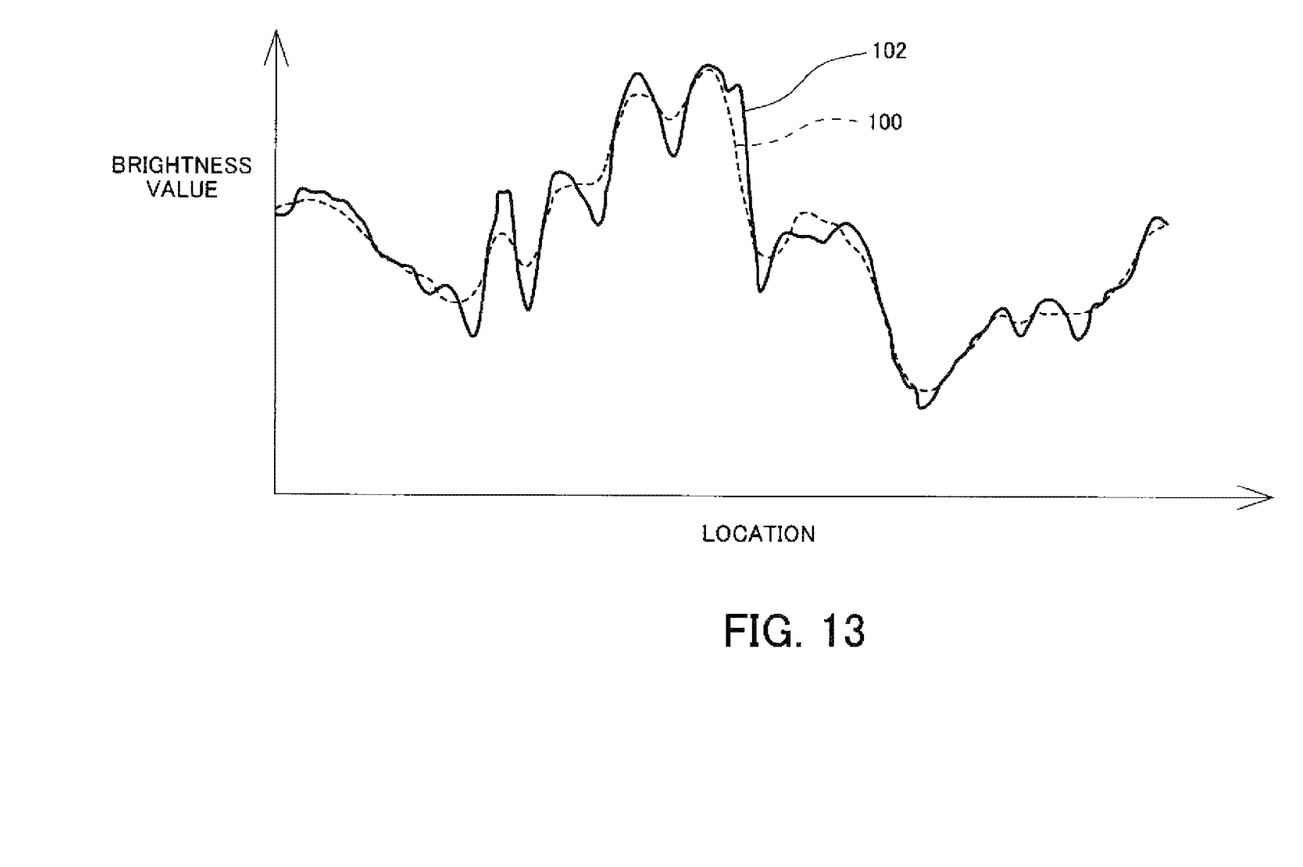
FIG. 13 is a view for explaining the operation of the directional interpolation processing according to the present embodiment.

FIG. 13 illustrates the effects of the post processing described above. In FIG. 13, the horizontal axis represents a location of a pixel and the vertical axis represents a brightness value. Numeral reference 100 represents a result of conventional non-directional linear interpolation processing, and numeral reference 102 represents a result of the directional interpolation processing according to the present embodiment. In the latter processing, unevenness is emphasized; particularly, the contour is emphasized, as illustrated, so that image quality is enhanced.

Figure 14:
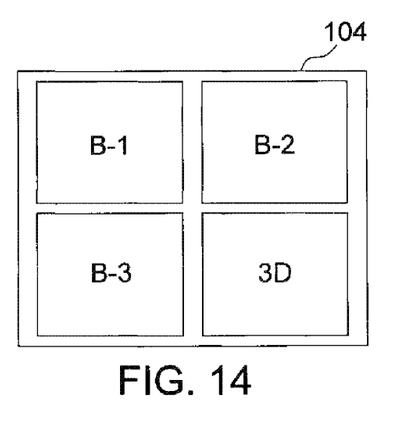
FIG. 14 illustrates four-view display.
Figure 15:
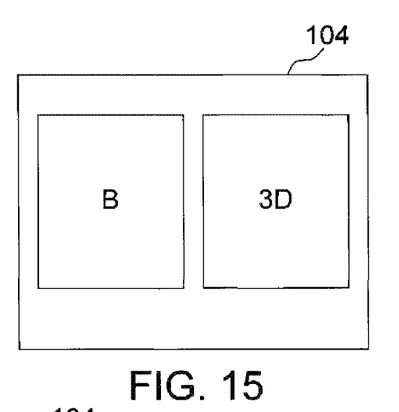
FIG. 15 illustrates two-view display.
Figure 16:
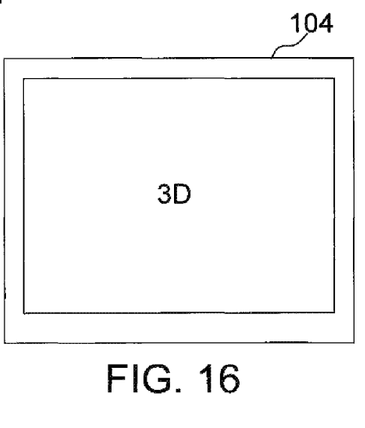
FIG. 16 illustrates one-view display.

FIG. 14 illustrates four-view display as an image to be displayed within the display screen 104. The four-view display is formed of a 3D image and three B-mode images. The three B-mode images are orthogonal to each other. FIG. 15 illustrates a two-view display which is formed of a 3D image and a single B-mode image. FIG. 16 illustrates a one-view display which is formed of a single 3D image. In the present embodiment, after formation of the three-dimensional image as illustrated in FIG. 4, for example, a slightly larger three-dimensional image as illustrated in FIG. 15 or a large three-dimensional image as illustrated in FIG. 16 can be configured. Specifically, it is possible to generate an enlarged three-dimensional image or a three-dimensional image having increased resolution in a simple manner, without increasing the number of rays. Further, control is performed such that the magnification is automatically changed in accordance with the number of views.

Although in the above embodiment the directional interpolation processing is applied to a three-dimensional image of a fetus, similar processing may be applied to other tissues. For example, the processing described above may be applied to a three-dimensional Doppler image representing blood flow. In this case, the directional interpolation processing may be applied to information of each color forming the three primary colors. Further, while contrast processing is applied after the directional interpolation processing in the above embodiment, the latter processing need not be always performed and may be applied as necessary.

While the preferred embodiment of the present invention has been described using specific terms, such description is for illustrative purposes only, and it is to be understood that changes and variations may be made without departing from the spirit or scope of the appended claims.

What is claimed is:

1. An ultrasound apparatus comprising:
an ultrasonic probe for capturing three-dimensional echo data;
a computer configured to process the captured three-dimensional echo data, wherein the computer operates in accordance with executable instructions, that, when executed, cause the computer to be configured as
a rendering processor which sets a plurality of rays with respect to volume data acquired from a three-dimensional space within a living organism and executes a rendering operation along each ray, to thereby generate an original image in the form of a three-dimensional image; and
a directional interpolation processor which generates a display image based on the original image, the directional interpolation processor applying directional interpolation processing on the basis of the original image to each of noted pixels forming the display image to generate an interpolated pixel value for the noted pixel,
wherein in the directional interpolation processing, a pixel reference direction for computing the interpolated pixel value is determined in a direction along a contour of a tissue which is three-dimensionally represented in the original image, and
the directional interpolation processor generates, as the display image, a first display image having a first resolution based on the original image in a first display mode, the first display image being a three-dimensional image in a four view display, and generates a second display image having a second resolution different from the first resolution based on the original image in a second display mode, the second display image being an enlarged or magnified image formed by the directional interpolation processing, and
by changing the magnification of the directional interpolation processing based on the number of views in the four view display, the first display image and the second display image are generated without changing the number of rays which are set with respect to the volume data beyond the number of rays used to generate the first display image.

2. The ultrasonic image processing apparatus according to claim 1, wherein
the computer that operates in accordance with the executable instructions to be configured as the directional interpolation processor is further configured in accordance with the executable instructions as
an evaluation value processor which sets a plurality of mutually different candidate directions on the original image, using a corresponding point corresponding to the noted pixel as a reference, and computes an evaluation value indicating a variation in pixel values in each of the candidate directions;
a direction determination processor which determines the pixel reference direction based on a plurality of evaluation values which are computed; and
an interpolated pixel value processor which computes the interpolated pixel value based on a plurality of pixel values concerning a plurality of pixels arranged in the pixel reference direction.

3. The ultrasonic image processing apparatus according to claim 1, wherein
as a result of applying the directional interpolation processing to each of pixels forming the first display image, the first image is generated, as a result of applying the directional interpolation processing to each of pixels forming the second display image, the second display image corresponding to an enlarged image of the first display image is generated, and an enlargement ratio of the second display image is determined based on the number of rays which is set for generating the original image.

4. The ultrasonic image processing apparatus according to claim 1, wherein the computer that operates in accordance with the executable instructions is caused to be further configured as
a post processor which applies post processing to the display image which is generated by the directional interpolation processing,
wherein the post processing is processing for adjusting a contrast of the display image.

5. The ultrasonic image processing apparatus according to claim 4, wherein
with the contrast adjusting processing, when an input pixel value is greater than a background average brightness value, based on the input pixel value, an output pixel value which is greater than the input pixel value is output, and when an input pixel value is smaller than the background average brightness value, based on the input pixel value, an output pixel value which is smaller than the input pixel value is output.

6. The ultrasonic image processing apparatus according to claim 1, wherein the volume data are volume data of a fetus.

7. An ultrasonic image processing method comprising:
capturing three-dimensional echo data with an ultrasonic probe;
setting a plurality of rays with respect to volume data acquired from a three-dimensional space within a living organism and executing a rendering operation along each ray using a computer, to thereby generate an original image in the form of a three-dimensional image; and
performing directional interpolation processing to generate a display image based on the original image, the directional interpolation processing applying directional interpolation processing on the basis of the original image to each of noted pixels forming the display image to generate an interpolated pixel value for the noted pixel,
the performing directional interpolation processing including:
setting a plurality of mutually different candidate directions on the original image, using a corresponding point corresponding to the noted pixel as a reference, and computing an evaluation value indicating a variation in pixel values in each of the candidate directions;
determining a pixel reference direction for computing an interpolated pixel value from among the plurality of candidate directions, based on a plurality of evaluation values which are computed; and
computing the interpolated pixel value based on a plurality of pixel values concerning a plurality of pixels arranged in the pixel reference direction,
wherein in the directional interpolation processing, the pixel reference direction is determined in a direction along a contour of a tissue which is three-dimensionally represented in the original image, and
the performing directional interpolation processing generates, as the display image, a first display image having a first resolution based on the original image in a first display mode, the first display image being a three-dimensional image in a four view display, and generates a second display image having a second resolution different from the first resolution based on the original image in a second display mode, the second display image being an enlarged or magnified image formed by the directional interpolation processing, and by changing the magnification of the directional interpolation processing based on the number of views in the four view display, the first display image and the second display image are generated without changing the number of rays which are set with respect to the volume data beyond the number of rays used to generate the first display image.

8. The ultrasonic image processing method according to claim 7, wherein in the directional interpolation processing, processing of changing a magnification or a resolution is executed simultaneously with the interpolation processing.

* * * * *